(12) United States Patent
Singh et al.

(10) Patent No.: US 8,389,640 B2
(45) Date of Patent: Mar. 5, 2013

(54) PROCESS FOR THE PREPARATION OF CROSS-LINKED POLYALLYLAMINE POLYMER

(75) Inventors: Girij Pal Singh, Pune (IN); Himanshu Madhav Godbole, Pune (IN); Umesh Babanrao Rananaware, Pune (IN); Vinayak Ravindra Sathe, Pune (IN); Sagar Purushottam Nehate, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 3 days.

(21) Appl. No.: 12/937,671

(22) PCT Filed: Jun. 23, 2008

(86) PCT No.: PCT/IN2008/000395
§ 371 (c)(1),
(2), (4) Date: Oct. 13, 2010

(87) PCT Pub. No.: WO2009/128085
PCT Pub. Date: Oct. 22, 2009

(65) Prior Publication Data
US 2011/0028660 A1   Feb. 3, 2011

(30) Foreign Application Priority Data

Apr. 15, 2008   (IN) .............................. 719/KOL/2008

(51) Int. Cl.
*C08F 16/00* (2006.01)

(52) U.S. Cl. .................................. 525/328.2; 525/359.3
(58) Field of Classification Search ............... 525/359.3, 525/328.2
See application file for complete search history.

(56) References Cited

U.S. PATENT DOCUMENTS

| | | | |
|---|---|---|---|
| 3,062,798 A | 11/1962 | Lovett | |
| 4,504,640 A | 3/1985 | Harada et al. | |
| 4,605,701 A | 8/1986 | Harada et al. | |
| 4,927,896 A | 5/1990 | Blocker et al. | |
| 5,496,545 A | 3/1996 | Holmes-Farley et al. | |
| 6,525,113 B2 | 2/2003 | Klix et al. | |
| 7,388,056 B2 * | 6/2008 | Gopalkrishna et al. | 525/359.3 |
| 2006/0258812 A1 | 11/2006 | Gopalkrishna et al. | |

FOREIGN PATENT DOCUMENTS

| | | |
|---|---|---|
| WO | WO 2005/015160 A2 | 2/2005 |
| WO | WO 2006/097942 A1 | 11/2006 |
| WO | WO 2007/070135 A1 | 6/2007 |
| WO | WO 2008/062437 | 5/2008 |

OTHER PUBLICATIONS

Davis et al., "Cyclodextrin-based pharmaceutics: Past, present and future," *Nature Reviews: Drug Discovery* (2004) 3: 1023-1035.
Kioussis et al., "Ammonium perchorlate-binding poly(allylamine hydrochloride) hydrogels for wastewater remediation," *Journal of Applied Polymer Science* (2001) 80: 2073-2083.

* cited by examiner

*Primary Examiner* — Edward Cain
(74) *Attorney, Agent, or Firm* — Merchant & Gould P.C.

(57) ABSTRACT

A process for the polymerization of allylamine and its subsequent crosslinking in the presence of a dispersing agent.

15 Claims, No Drawings

PROCESS FOR THE PREPARATION OF CROSS-LINKED POLYALLYLAMINE POLYMER

This application is a National Stage Application of PCT/IN2008/000395, filed Jun. 23, 2008, which claims benefit of Serial No. 719/KOL/2008, filed Apr. 15, 2008 in India and which applications are incorporated herein by reference. To the extent appropriate, a claim of priority is made to each of the above disclosed applications.

FIELD OF THE INVENTION

The present invention relates to a process for the preparation of a crosslinked polyallylamine polymer.

BACKGROUND OF THE INVENTION

Polyallylamine is a polymer of allylamine and comprises a long carbon chain with every alternate carbon bearing a pendant amino group. Each amino group is suspended from the chain by a methylene group and the polymeric structure can be represented as below.

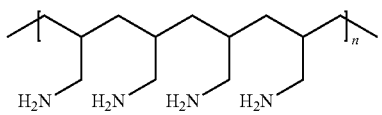

Polyallylamine can be crosslinked with itself (to form loops) or to other polyallylamine chains (to form ladder-like structures) or with other compounds through the amino groups. There are innumerable crosslinking agents known in the art ranging from the simple to the bulky, exemplary of which are 1,2 dichloroethane and sorbitol poly-glycidal ether. Depending on the requirements of the crosslinked polyallylamine the distance between the crosslinked chains can be manipulated effectively by judicious choice of the crosslinking agent.

The amino groups of polyallylamine also allow for further modification and functionalization. The combination of these functionalized amino groups and suitable crosslinking agents leads to endless possibilities and varieties of polyallylamine polymers. It is possibly this permutation that lends itself to the versatility of polyallylamine polymers for they are useful in fields as wide-ranging as waste-water treatment (*Journal of Applied Polymer Science*, 2001, 80, 2073) and pharmaceuticals. Polyallylamine linked with glucosyl or galactosyl moieties has been disclosed for the treatment of Diabetes, Metabolic syndrome and obesity in WO2007/070135. It has been linked to cyclodextrins for use as drug delivery vectors (*Nature Reviews: Drug Discovery* 2004, 3, 1023) and for the preparation of polymeric colloid nanoparticles—WO2005/015160. Polyallylamine crosslinked using epichlorohydrin has been approved by the U.S. FDA for therapeutic use in the treatment of chronic renal failure—Sevelamer, and for the reduction of elevated LDL cholesterol—Colesevelam. It also finds its uses in other fields like electrochemistry and as resins.

In 1985, the Japanese company, Nitto Boseki patented an industrial process to polymerize allylamine using Azo-compounds—U.S. Pat. No. 4,504,640 and the crosslinking of polyallylamine—U.S. Pat. No. 4,605,701. Allylamine can also be polymerized using tetraflurorohydrazine—$N_2F_4$ (U.S. Pat. No. 3,062,798) and with hydrogen peroxide in the presence of a multivalent metal ion (U.S. Pat. No. 4,927,896).

According to the crosslinking process of U.S. Pat. No. 5,496,545, an aqueous solution of polyallylamine hydrochloride is neutralized using sodium hydroxide and then the crosslinking agent, for example epichlorohydrin, is added to it. Within 15 minutes of the addition of epichlorohydrin the reaction mixture gels. The gel is cured for about eighteen hours at room temperature and then put in a blender to get coarse particles. The formation of a gel leads to handling difficulties and always necessitates blending to get the desired product.

When polyallylamine is crosslinked as described in U.S. Pat. No. 4,605,701, the polymer is obtained not as a gel, but as small globules. According to this process the crosslinking agent is added directly to the partially neutralized aqueous solution of polyallylamine hydrochloride. This process precludes gel formation by using a dispersing agent in the crosslinking step and stirring which results in the formation of small-globular polymer. However when this process is carried out on an industrial scale, the formation of a gel cannot be avoided entirely.

U.S. Pat. No. 6,525,113 describes a process for the preparation of crosslinked polyallylamine hydrochloride in which the swelling of the polymer is controlled. According to this process an aqueous solution of polyallylamine is first neutralized by using an alkoxide or a hydroxide. To this reaction mixture a water-miscible organic solvent is added. This solvent is said to displace the water out of the polyallylamine particles. The crosslinking agent is then added to the reaction mixture and the suspension that is formed after crosslinking is filtered to recover the product.

US 2006/258812 discloses a process for the preparation of a crosslinked polyallylamine polymer that has a particle size between 60 and 100 mesh. The process consists of adding the cross-linking agent to the aqueous solution of partially neutralized polyallylamine hydrochloride and dispersing the whole in an organic solvent that contains a surfactant. After a period of heating with concurrent stirring, the gel particles are isolated by filtration.

OBJECT OF THE INVENTION

It is thus an object of the present invention to provide a process for the preparation of a polymer that avoids the formation of a gel.

Another object is to provide a process that does not require the curing of the resultant product.

Yet another object of the invention is to provide a process that is practicable even on an industrial scale.

SUMMARY OF THE INVENTION

According to one aspect of the present invention there is provided a process for the polymerization of allylamine by treating an acid addition salt of allylamine in its solution of an acid with a radical initiator. According to another aspect of the present invention there is provided a process for preparation of a crosslinked polymer, said process comprising treating the polymer with a solution comprising crosslinking agent and dispersing agent.

According to a further aspect of the present invention there is provided a process for preparation of a crosslinked polymer, said process comprising treating a solution comprising the polymer and dispersing agent with cross linking agent.

DETAILED DESCRIPTION

The inventors have observed that the order of addition of the crosslinking agent and the dispersing agents affects formation of the gel with crosslinked polymers. The present inventors have minimized considerably the formation of a gel by allowing the reaction between polyallylamine (a polymer) and the crosslinking agent to occur strictly in the presence of a dispersing agent. The function of the dispersing agent is to promote the reaction between the polymer and the cross linking agent and to prevent gel formation. The technical advancement in the use of the dispersing agent resides in the simultaneous addition of the crosslinking agent and the dispersing agent to the polymer that is to be crosslinked. The simultaneous addition of the crosslinking agent and the dispersing agent to the reaction mixture can be elaborated to the manufacture of any polymer that is prepared in the form of a gel.

Allylamine is the monomer of the polymer polyallylamine. The preparation of polyallylamine by the polymerization of allylamine had been known to result in a polymer having a low degree of polymerization. However, the situation changed with the use of initiators bearing the azo group. Thus, to prepare polyallylamine, allylamine, which is a toxic liquid with a strong smell, is first converted into its salt. This can be done by dissolving allylamine directly in an acid. To this solution of an acid containing the allylamine salt, the solution of an Azo-based radical initiator can be added. Usually, the allylamine salt is separated from the acid in which it is dissolved before the radical initiator is added to it. However when the same has to be practiced on a large scale the isolation of the salt can be tedious and is inefficient in terms of the time involved and the energy consumed. (On a batch size of 40 kg, the time saved by not separating the allylamine salt or distilling off the excess solvent is between 24 and 28 hours.)

Consequently, the acid solution containing the allylamine salt is treated with the radical initiator and the polyallylamine polymer that is obtained is isolated and purified. The polyallylamine that is isolated is the corresponding acid salt of the allylamine that was used as starting material.

Before crosslinking, the polyallylamine salt is neutralized in order to free the amino groups. The polyallylamine salt is dissolved in an aqueous solution of a base such that it is neutralized partially. The crosslinking agent, for example epichlorohydrin, being insoluble in water, is dissolved in a hydrocarbon solvent. To this solution is added the surfactant or dispersing agent and the whole is added to the aqueous solution of polyallylamine. Alternatively, the crosslinking agent may be added to the solution containing the surfactant and polyallylamine. The reaction mixture is stirred, warmed and maintained for about 3 hours for the crosslinking to take place. The polymer that is formed is insoluble in most solvents and can be separated by filtration. Other methods of product isolation will be known to persons skilled in the art and can also be used. It is purified by washing with isopropanol several times and finally with demineralized water and dried. Isopropanol was the solvent chosen in order to remove the traces of epichlorohydrin. The product that is obtained in the end is a free-flowing powder.

Thus, according to the process of the current invention the polymer that is obtained need not be subjected to curing operations that consume time. The current process is quicker and more efficient. Also the polymer that is obtained by this process does not require further milling, grinding or blending. It can be used directly for all further processes and operations.

The process of the invention can be illustrated by the use of concentrated hydrochloric acid for polymerization and epichlorohydrin as the crosslinking agent in the preparation of Sevelamer.

EXAMPLES

Polymerization of Allylamine 200 mL of Conc. HCl was taken in a round-bottomed flask of 1 L capacity and cooled to less than 5° C. 100 g of allylamine was added slowly over a period of 1-1.5 hrs while stirring and maintaining the temperature at less than 10° C. After about 30 minutes the temperature of the reaction mixture was brought to room temperature. After another 30 minutes the temperature of the reaction mixture was raised to about 50° C.

20 g of 2,2-azobis-(2-amidinopropane) dihydrochloride was dissolved separately in 9 mL of demineralized water and warmed slightly to get a clear solution. This solution was added to the reaction flask containing allylamine. The reaction mixture was stirred for around 24 hours at 50-55° C. and a second aliquot (2 g) of 2,2-azobis-(2-amidinopropane) dihydrochloride was added to it. The reaction mixture was maintained for another 40-44 hours and then cooled to room temperature. It was then poured into 1.7 L of methanol in a nitrogen atmosphere. This solution was maintained at room temperature for 1 hour and filtered under vacuum in a nitrogen atmosphere. The product was washed with methanol and dried under vacuum.

Yield: 140 g

Crosslinking of Polyallylamine:

[a] With Sorbitan Sesquioleate.

27 g of NaOH was dissolved in 300 mL of demineralized water. 100 g of Polyallylamine hydrochloride was added to this solution at room temperature and stirred for about 45 minutes.

In another flask 4 mL of sorbitan sesquioleate was dissolved in 500 mL of toluene. This solution was subjected to charcoal treatment and 9 mL of epichlorohydrin was added to it. After 5-10 minutes the aqueous solution of polyallylamine was added to the toluene solution. The reaction mixture was stirred at room temperature for about 45 minutes and then heated to around 50° C. It was maintained at this temperature for about 2.5 hours and then cooled to room temperature.

The solid was collected by filtration and washed thoroughly with Isopropanol to remove traces of epichlorohydrin. After a final spray-wash with demineralized water the polymer was dried under vacuum.

Yield: ~750 g

[b] With Sorbitan Trioleate.

2.7 g of NaOH was dissolved in 30 mL of demineralized water. 10 g of Polyallylamine hydrochloride was added to this solution at room temperature and stirred for about 45 minutes.

In another flask 0.4 mL of sorbitan sesquioleate was dissolved in 50 mL of toluene. This solution was subjected to charcoal treatment and 0.9 mL of epichlorohydrin was added to it. After 5-10 minutes the aqueous solution of polyallylamine was added to the toluene solution. The reaction mixture was stirred at room temperature for about 45 minutes and then heated to around 50° C. It was maintained at this temperature for about 2.5 hours and then cooled to room temperature.

The solid was collected by filtration and washed thoroughly with Isopropanol to remove traces of epichlorohydrin. After a final spray-wash with demineralized water the polymer was dried under vacuum.

Yield: ~75 g

The invention claimed is:

1. A process for preparation of poly(allylamine-co-N,N'-dially-1,3-diamino-2-hydroxypropane), said process comprising:

neutralizing a polymer;

separately preparing a solution comprising crosslinking agent and dispersing agent;

adding the neutralized polymer to the solution and producing crosslinked-polymer in the form of a free flowing powder.

2. A process for preparation of poly(allylamine-co-N,N'-dially-1,3-diamino-2-hydroxypropane), said process comprising:

treating a solution comprising a polymer and dispersing agent with cross linking agent and producing crosslinked-polymer in the form of a free flowing powder.

3. The process according to claim 1 wherein the polymer to be crosslinked is polyallylamine.

4. The process according to claim 1 wherein the crosslinking agent is epichlorohydrin.

5. The process according to claim 1 wherein the dispersing agent is sorbitan sesquioleate.

6. The process according to claim 1 wherein the dispersing agent is sorbitan trioleate.

7. A process for the polymerization of allylamine by treating an acid addition salt of allylamine in its solution of an acid with a radical initiator.

8. The process according to claim 7, wherein the acid is hydrochloric acid.

9. The process according to claim 7, wherein the radical initiator contains an Azo group.

10. The process according to claim 9, wherein the radical initiator is 2,2-azobis-(2-amidinopropane).

11. A process for the preparation of poly(allylamine-co-N, N'-dially-1,3-diamino-2-hydroxypropane), the process comprising:

polymerizing allylamine hydrochloride salt to form polyallylamine hydrochloride;

partially neutralizing the resulting polyallylamine hydrochloride; and treating the neutralized polyallylamine hydrochloride with a solution comprising crosslinking agent and the dispersing agent.

12. The process according to claim 2 wherein the polymer to be crosslinked is polyallylamine.

13. The process according to claim 2 wherein the crosslinking agent is epichlorohydrin.

14. The process according to claim 2 wherein the dispersing agent is sorbitan sesquioleate.

15. The process according to claim 2 wherein the dispersing agent is sorbitan trioleate.

* * * * *